United States Patent

Beugelsdijk et al.

[11] Patent Number: 5,876,671
[45] Date of Patent: *Mar. 2, 1999

[54] SONICATION STANDARD LABORATORY MODULE

[75] Inventors: Tony Beugelsdijk; Robert M. Hollen; Tracy H. Erkkila; Lawrence E. Bronisz, all of Los Alamos; Jeffrey E. Roybal, Santa Fe, all of N. Mex.; Michael Leon Clark, Menan, Id.

[73] Assignee: The Regents of the University of California office of Technology Transfer, Alameda, Calif.

[*] Notice: Notice: The terminal 9 months of this patent has been disclaimed.

[21] Appl. No.: 454,057

[22] Filed: May 30, 1995

Related U.S. Application Data

[63] Continuation-in-part of Ser. No. 36,581, Mar. 24, 1993, abandoned.

[51] Int. Cl.[6] .......................... G01N 33/00; G01N 33/24; G01N 33/26
[52] U.S. Cl. ........................ 422/67; 422/63; 422/68.1; 422/99; 422/128; 436/31; 436/54; 436/57; 73/864.22; 73/863.23; 73/863.24
[58] Field of Search ............................. 422/63, 67, 68.1, 422/99, 128; 436/31, 57, 54; 73/864.22, 863.23, 863.24

[56] References Cited

U.S. PATENT DOCUMENTS

| | | | |
|---|---|---|---|
| 3,582,285 | 6/1971 | Hamilton | 23/259 |
| 3,899,376 | 8/1975 | Azarowicz | 435/262 X |
| 4,207,074 | 6/1980 | Suzuki | 436/54 X |
| 4,528,158 | 7/1985 | Gilles et al. | 422/63 |
| 4,654,171 | 3/1987 | Boncoeur et al. | 436/57 X |
| 4,720,374 | 1/1988 | Ramachanfran | 422/310 |
| 4,806,313 | 2/1989 | Ebersole et al. | 422/61 |
| 5,009,942 | 4/1991 | Benin et al. | 428/36.6 |
| 5,130,031 | 7/1992 | Johnston | 210/748 |
| 5,174,966 | 12/1992 | Durand et al. | 436/31 X |

Primary Examiner—Harold Y. Pyon
Attorney, Agent, or Firm—Milton D. Wyrick

[57] ABSTRACT

A standard laboratory module for automatically producing a solution of contaminants from a soil sample. A sonication tip agitates a solution containing the soil sample in a beaker while a stepper motor rotates the sample. An aspirator tube, connected to a vacuum, draws the upper layer of solution from the beaker through a filter and into another beaker. This beaker can thereafter be removed for analysis of the solution. The standard laboratory module encloses an embedded controller providing process control, status feedback information and maintenance procedures for the equipment and operations within the standard laboratory module.

2 Claims, 2 Drawing Sheets

SONICATION STANDARD LABORATORY MODULE

The present application is a continuation-in-part application out of U.S. patent application Ser. No. 08/036,581, filed Mar. 24, 1993, now abandoned.

FIELD OF THE INVENTION

The present invention generally relates to the field of chemical analysis of contaminants, and, more specifically, to robotic automation of chemical analysis of contaminants. The invention is a result of a contract with the Department of Energy (Contract No. W-7405-ENG-36).

BACKGROUND OF THE INVENTION

The past few years have seen a burgeoning of discoveries and revelations concerning environmental travesties, from illegal dumping of hazardous materials to oil spills, to decades old improper disposal of radioactive waste. Recently, facilities of the Department of Energy have been shown to have significant quantities of radioactive and hazardous wastes stored or buried on their premises. This has all led to great public awareness and concern over the long term effects of these actions, and to creating a political climate which is headed toward mandated remediation.

It is expected that the requirements for sampling and analysis of potentially contaminated soil and water will increase sharply as governmental agencies are required to devise and defend environmentally sound remediation programs. As an example, the Department of Energy currently is making between 2 and 3 million determinations per year. This figure is expected to grow to approximately 10 million determinations per year by 1995. At a current cost of about $300.00 per determination, the costs are becoming enormous, and represent a significant percentage of the DOE budget.

Due to the presence of radionuclides in much of the DOE waste, most commercial laboratories are not equipped to perform the required analytical processes. To perform this type of determination requires special facilities and a highly trained staff. Trained chemists with the requisite environmental chemistry experience are in short supply. These problems indicate that a chemistry vastly different from current practice is needed. The magnitude of the current problem dictates a production approach to its solution using technologies that will allow existing laboratories to operate continuously, instead of for only one-third of the day.

Solving these analysis problems is the mission of the current invention, as it is one component, known by the generic name of Standard Laboratory Module (SLM), in a system which will allow determination analyses to be performed continuously, with minimum operator involvement. A Standard Laboratory Module (SLM) refers to a self-contained assembly of components which will perform a subtask of a specific sample preparation method in a standardized modular fashion. Its function is basically to receive as input a bottle of a substance for extraction, to extract the substance, draw off a sample, filter out particulate matter, and deliver the liquid to be analyzed to an output container for transfer to the next module.

It is therefore an object of the present invention to present apparatus for the automated analysis of samples.

Additional objects, advantages and novel features of the invention will be set forth in part in the description which follows, and in part will become apparent to those skilled in the art upon examination of the following or may be learned by practice of the invention. The objects and advantages of the invention may be realized and attained by means of the instrumentalities and combinations particularly pointed out in the appended claims.

SUMMARY OF THE INVENTION

To achieve the foregoing and other objects, and in accordance with the purposes of the present invention, as embodied and broadly described herein, the apparatus of this invention comprises a standard laboratory module for producing a solution of contaminants for subsequent analysis comprising a first beaker for containing soil to be tested and sonication tip means for extending into and withdrawing from the first beaker, and for agitating a solution containing the soil to be tested. Control means are located in the standard laboratory module for providing process control, status feedback information, and maintenance of equipment and operations within the standard laboratory module. Sensing means determine the level of any of the soil in the first beaker in relation to the sonication tip means. Syringe pumps add chemicals to the first beaker. Pump means deliver a solvent to the first beaker. Aspirating tube means are connected to a vacuum source for drawing the solution of contaminants from the first beaker to a second beaker. Filtration means filter particulates from the solution of contaminates before the solution of contaminates enters the second beaker, the filtration means being a paper fiber membrane contained within a TEFLON® enclosure to prevent cross-contamination between different solutions of contaminants.

BRIEF DESCRIPTION OF THE DRAWING

The accompanying drawing, which is incorporated in and form a part of the specification, illustrates the embodiments of the present invention and, together with the description, serves to explain the principles of the invention. In the drawing.

DETAILED DESCRIPTION

Figure 1:
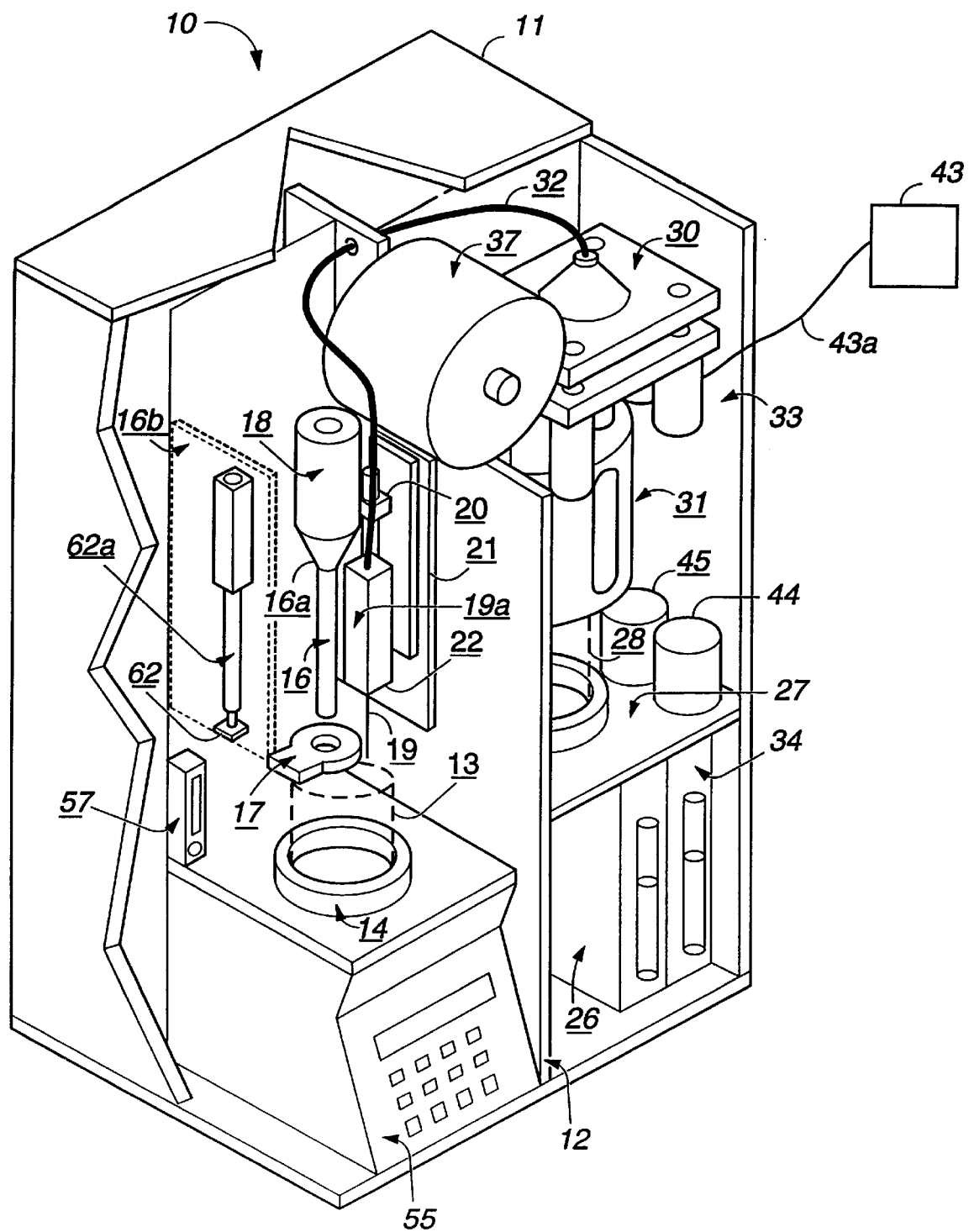
FIG. 1 is a perspective cutaway front_view of the major components of the present invention.

The present invention provides modular apparatus for the automated extraction of samples, and transfer of the produced liquid to an output beaker for later analysis by subsequent modules. The invention is best understood by reference to the drawings. In FIG. 1, a perspective cutaway plan view is illustrated wherein Standard Laboratory Module (SLM) 10 is contained within enclosure 11. Enclosure 11 also defines interior wall 12 onto which several components are mounted.

Beginning with the input to the SLM 10, input beaker 13 is shown in dashed lines in position on input platform 14, having been placed at that location either manually, or by a robotic arm (not shown). Input beaker 13 may typically be a 500 ml glass beaker. Below input platform 14, motor 15 is mounted for rotating input beaker 13. Input beaker 13 will have been placed into input platform 14 containing a sample to be analyzed, most likely a soil sample mixed with sodium sulfate. Extending through the solvent/rinse delivery ring 17, which is fixed to the interior wall of enclosure 11, is sonication tip 16. Sonication tip 16 is raised out of and lowered into input beaker 13 by the action of sonication tip linear-stage transport mechanism 16a, and its associated stepper-motor 16b.

Figure 2:
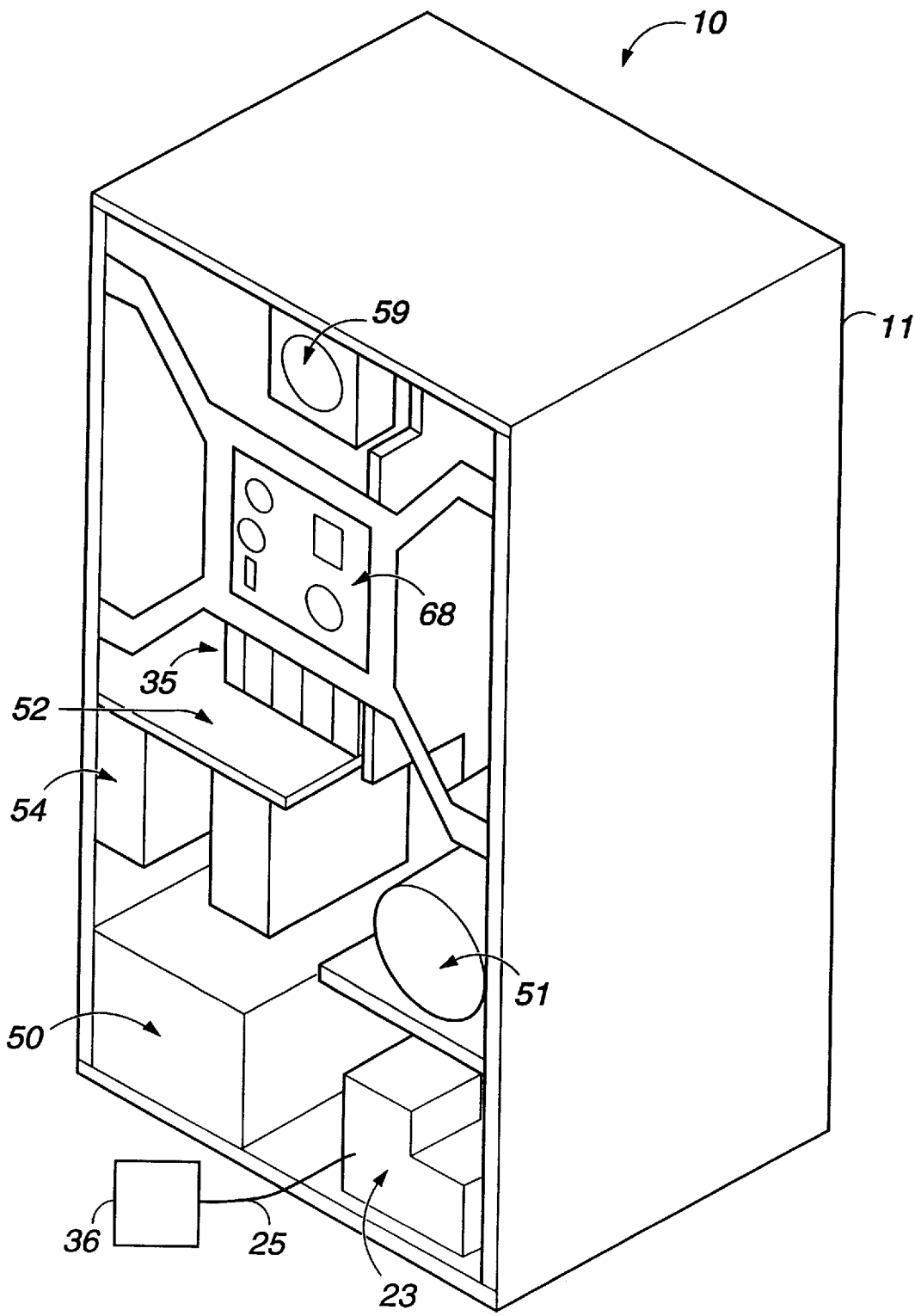
FIG. 2 is a perspective view of the rear of the present invention.

Referring now also to FIG. 2, solvent/rinse delivery ring 17 initially delivers a solvent solution, provided from metering solvent delivery pump 23 through tubing (not shown), to the sample in input beaker 13, beginning the dissolution of the sample. Sonication tip 16 then is activated through sonic energy generator 18 while input platform 14 is rotated to expedite extraction of the sample. Predetermined compounds, being any compounds employed by the user to aid in soil analysis, are stored in reservoir 44 and in reservoir 45. These predetermined compounds are not to interfere with the range and volatility of the soil to be tested. Individual tubing (not shown) transports the predetermined compounds from reservoir 44 and reservoir 45 to individual conventional syringe pumps. Both conventional syringe pumps are located below output beaker platform 27, from where the predetermined compounds, when required, can be injected directly into input beaker 13.

Aspirating tube 19 and its linear transport mechanism 20, and associated stepper motor 21 are mounted to interior wall 12. In operation, aspirating tube 19 is lowered into input beaker 13 and a portion of the solution is aspirated through aspirating tube 19, through tube 32 by evacuation of vacuum chamber 31. Rinse chamber pneumatic valve 22 is mounted below linear transport mechanism 20 and controls the flow of solvent from metering solvent delivery pump 23 through tubing to aspirating tube rinse chamber 19a, for cleansing aspirating tube 19, tube 32, and filtration mechanism 30.

At filtration mechanism 30, filter paper 37 is pulled though filtration mechanism 30, by a friction roller (not shown), which is driven by a stepper motor (not shown), and retained on a filter paper take-up roll (not shown). The filter paper advance is monitored by a paper encoder that compensates for changes in the diameter of the take up roll (not shown). Before a test, fresh filter paper is drawn into filtration mechanism 30, and later the soiled portion of the filter paper is moved onto the take-up roll.

Tubing (not shown) connects the lower output of filtration mechanism 30 to vacuum chamber 31. It is within vacuum chamber 31, with output beaker 28 inside vacuum chamber 31, that the solvent containing chemicals possibly removed from the soil under test is dispensed into output beaker 28.

Output beaker 28 is raised into vacuum chamber 31 and lowered for removal by way of pneumatic raise cylinders 26. In its lowered position, output beaker 28 can be removed either by manual or robotic means (not shown) for transport to a subsequent module for possible further testing or treatment.

The pneumatically operated components, namely pneumatic closing cylinder 62a, pneumatic raise cylinders 26, and rinse chamber pneumatic closing valve 22 are supplied with compressed gas with which to operate from pneumatic valves 34. Another pneumatic valve 34 is used for evacuating air from vacuum chamber 31. For the clarity of FIG. 1, the tubing connecting pneumatic valves 34 to pneumatic closing cylinder 62a, pneumatic raise cylinders 26, rinse chamber pneumatic closing valve 22 and vacuum chamber 31 are not shown.

Solvent for both dissolution of test samples, and cleaning of the components of the invention is provided from solvent reservoir 36. Solvent reservoir 36 is connected to metering solvent delivery pump 23 through tube 25. Metering solvent delivery pump 23 is responsible for delivering solvent to all necessary points within the module. In one application, the solvent in solvent reservoir 36 is 1, 1-dichloromethane ($CH_2Cl_2$). Solvent rinse waste from filtration mechanism 30 is directed through a valve (not shown) and tube 43a to waste reservoir 43.

The solvent flowing through aspirating tube 19 for cleansing is also drawn through tube 32 and into filtration mechanism 30 for cleansing from those components any residual contamination left from the preceding test.

For both sonication tip 16 and aspirating tube linear transport stages 19a, 20, optical proximity sensors (not shown) are employed to determine the home position and end limits of travel. Intermediate position is determined by optical encoders (not shown). The presence of output beaker 28, input beaker 13, and paper roll 37 are verified using reflectance/optical sensors (not shown). Magnetic proximity sensors (not shown) are used to verify that the position of output platform 27. The optical sensors are connected to optical proximity sensor amplifiers 35 which are in turn connected to embedded controller 50 (FIG. 2).

Soil level detector 62 consists of a reflectance sensor attached to the end rod of pneumatic cylinder 62a. The body of pneumatic cylinder 62a is attached to sonication tip linear transport stage 16a. When pneumatic cylinder 62a is actuated, the reflectance sensor of soil level detector 62 is positioned near the expected soil level in input beaker 13. Sonication tip linear transport stage 16a is lowered until the reflectance sensor detects the presence of soil. The encoder attached to sonication tip linear transport stage 16a is used to determine the soil height relative to sonicator tip 16.

The present invention can be utilized with and controlled by other contamination identification modules to which it is interfaced, or it can function independently through its embedded controller 50, which is located in the rear of SLM 10. Embedded controller 50 allows stand-alone operation of SLM 10, without integrating it with other instrumentation. It also provides optical and proximity sensor feedback monitoring to determine the status of SLM 10, and provides the capability to notify an operator of the status of the analysis operation.

Embedded controller 50 also has the capability of initiating appropriate events within SLM 10 to prevent a malfunction, or to halt the execution of SLM 10, should an un-recoverable malfunction occur, and to alter the execution sequence and timing for more flexible adaptation to different sample preparation schemes. Finally, embedded controller 50 provides for functional validation of SLM 10 by allowing an operator to step through any sequence of pre-programmed events and to validate that the steps are being executed correctly.

Keypad and display 55 operates in a testing mode to allow an operator to step through each function of SLM 10 utilizing a 486 operating system with software for running SLM 10. In the operating mode, keypad and display 55 and the operating system executes the function and monitors those functions with SLM 10 in operation. It also allow monitoring of the operation when SLM 10 is part of a larger system with other modules. The display also allows monitoring of the current status of SLM 10.

The following is a description of the process which is specified by EPA Method 3550, entitled *Sonication Extraction*. In summary, this method, to be practiced by the present invention, follows:

1. A 500 mL glass input beaker 13, containing 30 g of soil mixed with 60 g of sodium sulfate ($Na_2SO_4$) is placed onto input platform 14. A clean and empty 500 mL glass output beaker 28 is placed onto output beaker platform 27, and output beaker 28 is raised into vacuum chamber 31 by pneumatic raise cylinders 26. The pneumatic cylinder of soil level detector 62 is actuated, lowering its reflectance sensor to near the expected soil level. Sonication tip linear transport stage 16a is lowered slowly until the reflectance sensor detects the level of soil in input beaker 13. The position of the soil level relative to sonication tip 16 is determined from sonication tip linear transport stage 16a is determined from the encoder associated with sonication tip linear transport stage 16a. This process is repeated three (3) times to determine an average soil height.

2. One (1) mL of a spike solution and one (1) mL of a surrogate solution, if appropriate for the test, are dispensed into input beaker 13 through syringe pump dispensing tips (not shown).

3. Metering peristaltic solvent delivery pump 23 then delivers 70 mL of 1, 1-dichloromethane ($CH_2Cl_2$) solvent from solvent reservoir 36 to input beaker 13 through horn rinse ring 17.

4. Sonication tip 16 is next lowered into input beaker 13 by sonication tip linear stage transfer mechanism 16a to approximately 2 mm above the soil level determined in step number 1. The motor (not shown) below input platform 14 then rotates input platform 14, and sonication tip 16 is engaged at a 50% duty cycle and at one-half total output power for two minutes.

5. The rotation of input beaker 13 is stopped, and sonication tip 16 is raised and rinsed with approximately 5 mL of solvent.

6. Filter paper (Whatman Type 41) from filter paper supply roll 37 which is inside filtration mechanism 30 is rinsed twice with solvent, and the rinse waste is directed through a valve and tube 43a to waste reservoir 43.

7. The slurry in input beaker 13 is allowed to settle for one (1) minute.

8. Aspirating tube 19 is then lowered into input beaker 13 and the top layer of solvent (above the settled soil) is aspirated through aspirating tube 19, through tube 32, through the filter paper in filtration mechanism 30, and into output beaker 28 by way of evacuation of vacuum chamber 31.

9. Aspirating tube 19 is then withdrawn from input beaker 13, and into aspirating tube rinse chamber 19a, where it is twice rinsed with 7 mL of solvent. This is done with vacuum chamber 31 still evacuated, so the solvent also rinses tube 32, and flows into output beaker 28.

10. The filter paper is advanced though filtration mechanism 30 by a friction roller and its associated stepper motor.

11. Steps 3–10 are repeated two more times.

12. Output beaker 28 is then lowered by pneumatic raise cylinders 26 and is ready for pick up.

13. Input beaker 13 is then ready to be picked up.

The foregoing description of the preferred embodiments of the invention have been presented for purposes of illustration and description. It is not intended to be exhaustive or to limit the invention to the precise form disclosed, and obviously many modifications and variations are possible in light of the above teaching. The embodiments were chosen and described in order to best explain the principles of the invention and its practical application to thereby enable others skilled in the art to best utilize the invention in various embodiments and with various modifications as are suited to the particular use contemplated. It is intended that the scope of the invention be defined by the claims appended hereto.

What is claimed:

1. A standard laboratory module for producing a solution of contaminants for subsequent analysis comprising:

a first beaker for containing soil to be tested to a level within said first beaker;

sonication tip means removably extended into said first beaker, for agitating a solution containing said soil to be tested;

a platform supporting said first beaker and a stepper motor connected to said platform for rotating said first beaker while said sonication tip means is extended into said first beaker;

control means located in said standard laboratory module for providing process control, status feedback information and maintenance of equipment and operations within said standard laboratory module;

a sensor attached to a pneumatic sensor coupled with a transport platform for determining said level of any of said soil in said first beaker in relation to said sonication tip means;

syringe pumps for adding predetermined compounds to said first beaker;

pump means for delivering a solvent to said first beaker aspirating tube means connected to a vacuum source for drawing said solution of contaminants from said first beaker to a second beaker; and filtration means for filtering particulates from said solution of contaminates before said solution of contaminates enters said second beaker, said filtration means being a roll of filter paper incrementally advanced by a drive roller coupled to a stepper motor contained within an enclosure made of tetrafluoroethylene fluorocarbon polymers to prevent cross-contamination between different solutions of contaminants.

2. The apparatus as described in claim 1 wherein said pump means also delivers solvent to said aspirating tube means for cleaning said aspirating tube means and said filtration means.

* * * * *